(12) United States Patent
Colpaert et al.

(10) Patent No.: US 8,106,074 B2
(45) Date of Patent: Jan. 31, 2012

(54) PYRIDIN-2-YL-METHYLAMINE DERIVATIVES FOR TREATING OPIATE DEPENDENCE

(75) Inventors: Francis Colpaert, Puylaurens (FR); Liesbeth Bruins Slot, Castres (FR); Gilbert Alphonse Morales, legal representative, Garrigue (FR); Wouter Koek, San Antonio, TX (US); Jean-Pierre Tarayre, Castres (FR); Bernard Vacher, Castres (FR)

(73) Assignee: Pierre Fabre Medicament, Boulogne (FR)

( * ) Notice: Subject to any disclaimer, the term of this patent is extended or adjusted under 35 U.S.C. 154(b) by 479 days.

(21) Appl. No.: 12/328,280

(22) Filed: Dec. 4, 2008

(65) Prior Publication Data
US 2010/0099709 A1 Apr. 22, 2010

Related U.S. Application Data

(63) Continuation-in-part of application No. 10/483,567, filed on Nov. 3, 2004, now abandoned.

(30) Foreign Application Priority Data

Jul. 13, 2001 (FR) ...................................... 01 09350

(51) Int. Cl.
*A61K 31/445* (2006.01)
(52) U.S. Cl. ...................................................... 514/318
(58) Field of Classification Search .................... 514/318
See application file for complete search history.

(56) References Cited

U.S. PATENT DOCUMENTS

| 5,741,789 | A | 4/1998 | Hibschman et al. |
| 5,929,078 | A | 7/1999 | George et al. |
| 6,020,345 | A | 2/2000 | Vacher et al. |

FOREIGN PATENT DOCUMENTS

| EP | 0928792 | 7/1999 |
| EP | 0982030 | 3/2000 |
| WO | WO-94/29293 | 12/1994 |
| WO | WO-97/02269 | 1/1997 |
| WO | WO-97/03071 | 1/1997 |
| WO | WO-97/06155 | 2/1997 |
| WO | WO-97/17343 | 5/1997 |
| WO | WO-97/23485 | 7/1997 |
| WO | WO-97/30050 | 8/1997 |
| WO | WO-97/41858 | 11/1997 |
| WO | WO-98/08817 | 3/1998 |
| WO | WO-98/22459 | 5/1998 |
| WO | WO-98/42344 | 10/1998 |
| WO | WO-99/38864 | 8/1999 |
| WO | WO-00/00196 | 1/2000 |
| WO | WO-00/35874 | 6/2000 |
| WO | WO-00/35875 | 6/2000 |
| WO | WO-00/35878 | 6/2000 |
| WO | WO-00/35892 | 6/2000 |

OTHER PUBLICATIONS

Patani, George A. Bioisosterism: A rational approach in drug design. Chem. Rev. 96 (1996) 3147-3176.*
Berthold, H. et al. "Mechanism of the Attenuation of Naloxone-Induced Jumping Behavior in Morphine Dependent Mice by 5 HT-1 Receptor Agonists," *British Journal of Pharmacology*, vol. 95 p. 869, (1988).
Gonzalez, J.P. et al. "Behavioral Effects of 5 Hydroxytyptamine-$_1$ and 5-Hydroxytryptamine-$_2$ Agonists on Naloxone Precipitated Morphine Abstinence," *British Journal of Pharmacology*, vol. 86 p. 444, (1986).
Gulati, A. et al. "Down-Regulation of Hypothalamic 5 HT-$_{1A}$ Receptors in Morphine-Abstinent Rats," *EP Journal of Pharmacology*, vol. 182. No. 2 pp. 253-260, (1990).
Vacher, B. et al. "Novel Derivatives of 2-Pyridinemethylamine as selective, Potent and orally Active Agonists at 5-HT 1A receptor," *J. Med. Chem.*, vol. 42, pp. 1648-1660, (1999), American Chemical Society.
Millan, M. J. et al. "Apparent hyperalgesic action of the 5-HT$_{1A}$ agonist, 8-OH-DPAT, in the rat reflects induction of spontaneous tail-flicks," *Neuroscience Letters*, vol. 107, Issues 1-3, pp. 227-232, (1989), Elsevier Science Ireland Ltd.
Millan, M.J. et al., "5-Hydroxytryptamine (HT) 1A receptors and the tail-flick response", *Journal of Pharmacology and Experimental-Therapeutics*, vol. 256, No. 3, pp. 983-992, (1991), American Society for Pharmacology and Experimental Therapeutics.
Bruins Slot, L.A. et al. "Sign-Reversal During Persistent Activation in μ-Opioid Signal Transduction", *J. Theor. Biol.* 215, pp. 169-182, (2002), Elsevier Science Ltd.
Colpaert F.C. et al. "Opiate Self-Administration as a Measure of Chronic Nociceptive Pain in Arthritic Rats", *International Association for the Study of Pain*, vol. 91, pp. 33-45, (2001) Elsevier Science B.V.
Suzuki et al. "Role of the Kappa-Opioid System in the Attenuation of the Morphine-induced place preference under chronic pain,"(abstract), *Life Sci.* 64(1): PL1-7, (1999).
Suzuki et al. "Mechanism of opioid dependence and interaction between opioid receptors", (abstract) *Eur. J. Pain*, vol. 5, Suppl. A, pp. 63-65, (2001).

(Continued)

*Primary Examiner* — Rebecca Anderson
*Assistant Examiner* — Samantha Shterengarts
(74) *Attorney, Agent, or Firm* — Buchanan Ingersoll & Rooney PC

(57) ABSTRACT

The invention concerns the use pf compounds of general formula (I)

(I)

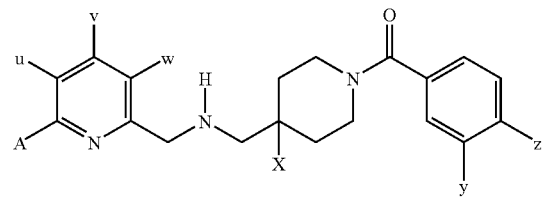

for treating opioid drug dependence, hyperalgesia induced by opiate drug withdrawal and psychological craving induced by opiate drug withdrawal.

16 Claims, 1 Drawing Sheet

OTHER PUBLICATIONS

Rawls et al. "Agmatine blocks morphine-evoked hyperthermia in rats," *Brain Research*,1147, pp. 89-94, (2007), Elsevier B.V.

Colpaert et al. "High-Efficacy 5-Hydroxytryptamine 1A Receptor Activation Counteracts Opioid Hyperallodynia and Affective Conditioning," *J. Pharmacology and Experimental Therapeutics*, vol. 316, No. 2, pp. 892-899, (2006).

Craig, A.D. "A New View of Pain as a Homeostatic Emotion", *Trends in Neurosciences*, vol. 26, No. 6 pp. 303-307, (2003), Elsevier Science Ltd.

Hunt, S. et al. "The Molecular Dynamics of Pain Control," *Nature Reviews/Neuroscience* vol. 2, pp. 83-90, (2001) Macmillan Magazines, Ltd.

Tilson, H.A. et al. "Hyperalgesia During Withdrawal as a Means of Measuring the Degree of Dependence in Morphine Dependent Rats," *Psychopharmacologia(Berl.)* vol. 28, pp. 287-300, (1973), Springer-Verlag.

Sleight, A. et al. "Identification of 5-Hydroxytryptamine $_{1A}$ Receptor Agents Using a Composite Pharmacophore Analysis and Chemical Database Screening" *Naunyn-Schmiedeberg's Archives of Pharmacology* vol. 343, pp. 109-116 (1991) Springer-Verlag.

Colpaert, F. "System Theory of Pain and of Opiate Analgesia: No Tolerance to Opiates," *Pharmacological Review*, vol. 48 No. 3, pp. 355-402; (1996), The American Society for Pharmacology and Experimental Therapeutics.

Randall, L. et al. "A Method for Measurement of Analgesic Activity on Inflamed Tissue" *Arch. Inst. Pharmacodyn.*, No. 4, CX1, pp. 409-419, (1957) Hoffmann-La Roche, New Jersey.

International Search Report for PCT/FR02/02449 dated Nov. 20, 2002.

\* cited by examiner

FIG. 1. Effect of compound F on morphine dependence
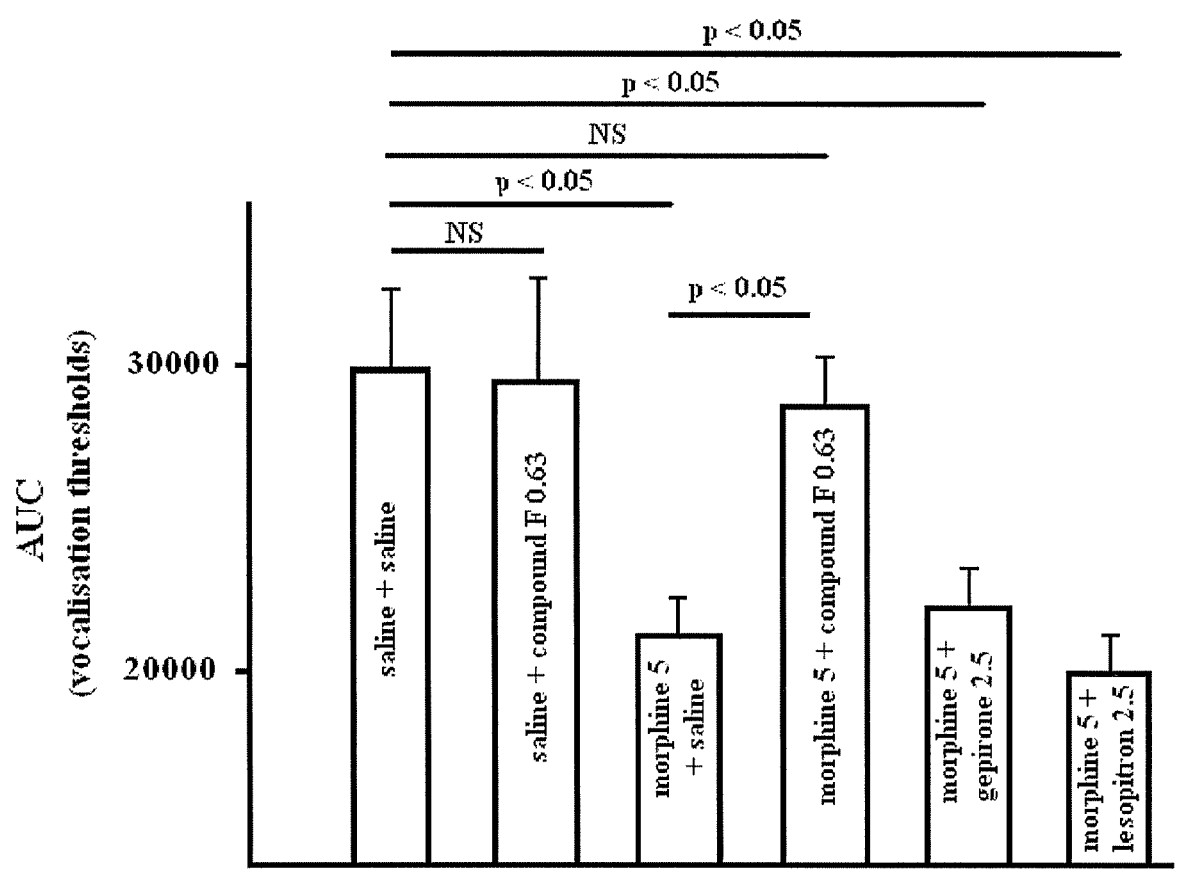
NS: non-significant difference
p<0.05: *post-hoc* comparisons
with the Student Newman Keuls test

PYRIDIN-2-YL-METHYLAMINE DERIVATIVES FOR TREATING OPIATE DEPENDENCE

The present patent application is a continuation in part of U.S. application Ser. No. 10/483,567 filed on Nov. 3, 2004, claiming the priority of FR0109350 from Jul. 13, 2001, and incorporated herein by reference.

The aim of the present invention is a new utilisation of certain compounds of pyridin-2-yl-methylamine for the treatment of drug dependence (in other terms: "drug addiction", "drug abuse").

Drug dependence on a psycho-active substance is a pathological phenomenon, classified among mental troubles in the international classification of the World Health Organisation. The list of substances producing a drug dependence or dependence syndrome is long. However, the field of application of the present invention is limited to the treatment of opiate drug dependence. By opiates, the inventors mean natural, semi-synthetic or synthetic compounds as a whole, having a morphine-like activity.

The principle for treating drug dependence is based on enabling the dependent subject to become, and then to remain, abstinent from the substance on which he or she is dependent. In the particular case of opiate dependence, the pharmacological treatments in use are so-called substitutive treatments. Their principle consists in replacing the substance or substances responsible for the dependence by an opiate product with lower specific effects and with a longer active period than those of the substance(s) responsible for the dependence. The medicaments available in the substitution indication are, according to the country, methadone chlorhydrate, levo-alpha-acetylmethadol (LAAM) and buprenorphine. However, the success rate of these treatments is limited. In addition, since the products used in substitution treatments belong themselves to the pharmacological opiate class, they also pose a direct or indirect risk for public health. Thus, substitution products can in turn induce a dependence syndrome and/or increase the risk of abuse and dependence on other substances such as, for example, cocaine. Conjointly with substitution treatments, certain agonists of noradrenaline $\alpha_2$ receptors, such as clonidine and iofexidine are sometimes also used in support and prevention treatment for relapses after opiate withdrawal therapy.

Current treatments for opiate drug dependence are therefore not entirely satisfactory. As a result, the discovery of new treatments involving molecules with a mechanism action different from that of existing products is highly desirable.

The mechanisms underlying the dependence syndrome are complex and, as a result, difficult to determine. In fact, different classes of receptors and neurotransmitters are involved. Nonetheless it seems to be established that dopamine plays a central role. It is also evident that noradrenaline and serotonin, which among other things act as modulators and/or regulators of dopaminergic neuron activity in the cerebral areas involved in dependence phenomena, constitute privileged targets for therapeutic interventions.

Colpaert et al. (Pharmacol Rev 48: 355-342, 1996) and Bruins Slot et al. (J Theor Biol 215:169-182, 2002) hold that any opiate treatment induces, directly or indirectly, two opposite affective effects: on the one hand, opiate treatment directly induces analgesia and a more or less intense euphoric (positive-affect) state that is believed to constitute a direct effect that may nonetheless also be associated with the alleviation of pre-existing pain. On the other hand, when opiate effects diminish in the body (naturally, or upon drug withdrawal), arises a state of pain or of "hyperalgesia" (negative-affect), which corresponds to an increased sensitivity to pain (in other terms: "hyper-allodynia", "dysphoria" or "pain"). Such pain/hyperalgesia may occur even after a first administration, however low its dose and however short its duration is. The opiate-induced pain/hyperalgesia is as robust as opiate-induced analgesia/hypo-algesia, and increases with prolonged or repeated opiate treatment.

Pain encompasses, and can be identified by, both its sensory ("physiological") and psychological affective/motivational ("pathological") dimensions (Craig, 2003, Trends Neurosci 26:303-307; Hunt and Mantyh, 2001, Nature Rev Neurosci 2:83-91); indeed, pain both hurts and makes one suffer. Like hunger and thirst, pain constitutes a powerful motivational drive that leads to compulsive opiate use (dependence): as a matter of fact, opiate-induced pain makes the subject "crave" for a further opiate administration which will, at first, relieve the pain by inducing temporarily analgesia. However, opiate-induced pain will then appear again with a now increased severity, and the subject, taken in this vicious circle, will become even more addicted to the opiate treatment.

Thus, opiate-induced pain triggers the opiate-associated craving and dependence. In fact, pain/hyperalgesia is since long considered as a marker of opiate dependence (Tilson et al., Psychopharmacol 28:297-300, 1973).

Craving is a compelling drive for auto-medication. It appears when the drug causing the dependence is discontinued or decreased in dosage. Such symptoms are either physiological or psychological. Physiological symptoms (also called "physical dependence") encompass body weight loss, hypothermia, pallor, diaphoresis, tachycardia, hypertension, lightheadedness, nausea, wet dog shakes, mastication, squealing, diarrhea and fainting.

However, psychological craving (addiction) is to be carefully distinguished from physical dependence. Craving is a psychological compulsion to use a drug—in spite of the harm that such produces—, a compulsion that often persists long after the physical withdrawal symptoms have abated. Thus, psychological craving is a phenomenon that lasts much longer than the physiological dependence, and is far more dangerous for a patient to become dependent again. Alleviating this particular symptom is therefore a prerequisite for successfully stopping drug intake and for the long-lasting counteraction of opiate dependence. Treatment of psychological craving eventually leads to the alleviation of drug dependence.

However, to date, no treatment has been described for alleviating opiate-induced pain/hyperalgesia and psychological craving, thereby reducing drug addiction/dependence.

In fact, the existence of a link between certain sub-types of the serotonine bond site, including the 5-HT$_{1A}$ sub-type among others, and morphine dependence, has been discussed in scientific reports since the end of the '80s. Consecutively, the potential field of application of compounds with an affinity for the 5-HT$_{1A}$ receptor has, more or less systematically, been extended to treating withdrawal syndrome and/or abuse and/or drug dependence on psycho-active substances, including ethanol and nicotine.

Thus, in the European patent application EP 356997, the firm of Bristol-Myers Co. claims the use of azapirones such as, for example, buspirone, in treating abuse of psycho-active substances in general, as well as over-eating syndromes.

In international applications WO 0035892, WO 0035874, and WO 0035878, the firm of American Home Products Corporation describes derivatives of piperazine-ethylamides, aryl-piperidines and 1,4-piperazines respectively, as agonists and antagonists of the 5-HT$_{1A}$ receptor, useful in treating drug habituation. These statements are not supported by any experimental results, but are rather grounded on the fact that, as agonists and antagonists of the 5-HT$_{1A}$ receptor, these molecules may act somehow on the central nervous system, and, as such, may help treating depression, anxiety, panic, obsessive-compulsive disorders (OCD), sleep disorders, sexual dysfunction, alcohol and drug addiction, cognition enhancement, Alzheimer's disease, Parkinson's disease, obesity and migraine. Therefore, treating drug addiction is not the specific aim of molecules that act on the 5-HT$_{1A}$ receptor. Moreover, without any experimental results showing this particulate point, it is difficult to imagine that the 5-HT$_{1A}$ receptor molecules might be able to treat with equal efficacy all the above-mentioned diseases.

Such an ungrounded teaching is also disclosed in:

The international application WO 9938864, describing derivatives of oxazoles as agonists of the receptor 5-HT$_{1A}$ useful in treating withdrawal syndrome and habituation to drugs.

The applications WO 9808817 and WO 9717343, describing derivatives of 4-aminoethoxy-indoles and benzodioxane-methylamines, respectively, as ligands of the 5-HT$_{1A}$, receptor useful in treating abuse and dependence.

The international application WO 0035875, derivatives of aryl-piperidines describing antagonists of the 5-HT$_{1A}$ receptor useful for treating drug habituation.

The international applications WO 9723485, WO 9702269, WO 9703071, wherein the Knoll company claims derivatives of heteroaryl-carboxamides, of thiazoles, and of heterocyclyl-carboxamides, respectively, as non-selective ligands of the 5-HT$_{1A}$ receptor useful in treating abuse of and habituation to psycho-active substances.

The international application WO 9730050, wherein the Pharmacia & Upjohn S.P.A. company reports derivatives of heterocyclyl-ergolines as selective ligands of the 5-HT$_{1A}$ receptor useful in treating drug withdrawal and habituation;

The applications EP 982030 and EP 928792, wherein the company of Pfizer Products Inc. discloses derivatives of 2,7-substituted-octahydro-pyrrolo-1,2-pyrazines and Bicyclo (3.1.0.) hexanes, respectively, as ligands of the 5-HT$_{1A}$ receptor useful in the treatment of dependence.

The international application WO 9842344, wherein the company of R. P. Scherer Limited claims the utilisation of a pharmaceutical composition comprising a 5-HT$_{1A}$ agonist such as, for example, buspirone, in the treatment of abuse and habituation to certain substances.

The international application WO 9706155, wherein the Synthélabo company discloses derivatives of naphthalen-1-yl-piperazines as ligands of the 5-HT$_{1A}$ receptor useful in treating problems due to withdrawal or to the abuse of stupefacient.

The application WO 9429293 the firm of Yamanouchi Pharm Co Ltd reports derivatives of fluoro-chromanes as being ligands of the 5-HT$_{1A}$ receptor useful in the treatment of drug dependence.

Other applications, although claiming the use of a 5-HT$_{1A}$ receptor ligand for treating drug addictions in general, have succeeded in proving the efficiency of the 5-HT$_{1A}$ receptor ligand specifically on tobacco or alcohol dependence. For example, the application WO 9741858, discloses experimental results showing that derivatives of piperazines are efficient in treating alcoholic dependence in rats. Moreover, in the application U.S. Pat. No. 5,741,789, the firm of Eli Lilly and Company describes hetero-oxy-alkanamines, agonists or partial agonists of the 5-HT$_{1A}$ receptor, as being useful in treating tobacco addiction. Finally, in the international application WO 0000196, the same firm describes pyrrolidines and pyrrolines, non-selective antagonists of the 5-HT$_{1A}$ receptor, as being useful in the treatment of the abuse of tobacco. However, as they are dedicated to alcoholic or tobacco dependence treatment, there is no experimental data in these applications concerning opiate dependence.

In general, it is noteworthy that the actual effect of 5-HT$_{1A}$ agonists on opiate dependence is never shown nor suggested in any of the above-mentioned patent applications.

Moreover, while alcohol and tobacco are often included in listings of abused and/or addicting substances, it would not be obvious beforehand that an agent useful in treating alcohol or tobacco abuse would also find use in treating the addiction to substances such as opiates. As a matter of fact, opiate addiction is far more difficult to overcome than alcohol and tobacco dependence, obviously because withdrawal syndromes associated with opiate craving are different from and likely more profound and long-lasting than the ones induced by tobacco and alcohol.

Finally, the 5-HT$_{1A}$ agonists tested clinically in treating dependence for such addictive/dependence-inducing drugs as, for example, cocaine, have provided negative results (Berthold H et al, British Journal of Pharmacology, vol. 95, pp. 869, 1988). Furthermore, if anything, the latter article discourages one of ordinary skill in the art from seeking new 5-HT$_{1A}$ agonists for the treatment of drug dependence.

Hence, according to the present state of the art, the potential utility of new 5-HT$_{1A}$ agonists in the treatment of opiate drug dependence in particular is difficult to predict.

BRIEF DESCRIPTION OF THE DRAWINGS

FIG. 1 shows the effect of compound F on morphine dependence.

The inventors have discovered, unexpectedly, that the compounds claimed by the applicant in patent WO 98/22459 and represented by the general formula (I):

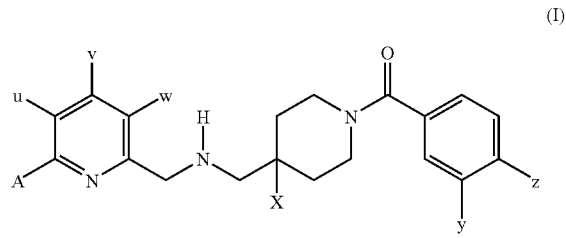

in which:

u represents a hydrogen atom or a methyl radical with the proviso that when u is a methyl radical then v and w represent a hydrogen atom;

v represents a hydrogen atom, a chlorine atom or a methyl radical with the proviso that when v is a methyl radical then u and w represent a hydrogen atom;

w represents a hydrogen atom, a fluorine atom or a methyl radical with the proviso that when w is a methyl radical then u and v represent a hydrogen atom;

x represents a hydrogen atom or a fluorine atom;

y represents a chlorine atom or a methyl radical;

z represents a hydrogen atom or a fluorine atom or a chlorine atom or a methyl radical;

A represents:
a hydrogen atom or a fluorine atom or a chlorine atom;
an alkyl radical in $C_1$-$C_5$, i.e. a straight or branched chain saturated aliphatic hydrocarbon radical containing from 1 to 5 atoms of carbon such as methyl, ethyl, propyl, butyl, pentyl, isopropyl, 1-methyl-ethyl, 1-methyl-propyl, 1-methyl-butyl, 2-methyl-propyl, 2-methyl-butyl or 3-methyl-butyl, 1-ethyl-propyl, 2-ethyl-propyl;
a fluoroalkyl radical such as monofluoromethyl (—$CH_2F$) or difluoromethyl (—$CHF_2$) or trifluoromethyl (—$CF_3$) or 1-fluoro-1-ethyl (—$CHFCH_3$) or 1,1-difluoro-1-ethyl (—$CF_2CH_3$);
a cyclopropyl or cyclobutyl or cyclopentyl radical;
an 5-membered aromatic heterocyclic group, substituted or not, containing 1, 2, 3 or 4 heteroatoms chosen from amongst nitrogen, oxygen and sulphur but nonetheless without more than one oxygen and/or sulphur atom being present in the heterocycle A.
an alkoxy ($R_1O$—) or alkylthio ($R_1S$—) group in which the $R_1$ radical represents:
an alkyl radical in $C_1$-$C_5$ such as defined above;
a monofluoromethyl or trifluoromethyl radical;
a cyclopropyl or cyclobutyl or cyclopentyl radical;
an amino group of type II

(II)

in which $R_2$ and $R_3$, identical or different, represent hydrogen or an alkyl radical in $C_1$-$C_5$ such as defined above or a cyclopropyl group or a trifluoromethyl group;
a saturated cyclic amino group of type III

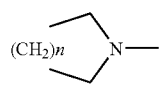
(III)

in which n can be the integers 1 or 2;
an alkoxycarbonyl group, preferably a methoxycarbonyl ($CH_3OCO$—) group or an ethoxycarbonyl ($CH_3CH_2OCO$—) group; as well as its addition salts with pharmaceutically acceptable organic or mineral acids are, unexpectedly, efficient in treating opiate drug dependence.

The compounds of formula (I) are known to be selective agonists of 5-$HT_{1A}$ receptors and their uses in other medical fields are described in the international application WO 98/22459. For example, WO 98/22459 discloses the potential use of compounds of formula (I) for treating depression, anxiety, panic, obsessive-compulsive disorders (OCD), sleep disorders, sexual dysfunction, pain perception (nociception), vomiting, gastric secretion, food uptake, immune diseases, vascular disorders such as arterial hypertension or migraine. Hence, it is not described nor suggested in WO 98/22459 the use of compounds of formula (I) for treating drug dependence.

Preferably, in the present invention, the compound of formula (I) is (3-Chloro-4-fluorophenyl)-(4-fluoro-4-{[(5-methyl-pyridin-2-yl-methyl)-amino]-methyl}-piperidin-1-yl)-methadone fumarate, that is: A=H, u=$CH_3$, v and w=H, x=F, y=Cl and z=F in the general formula (I). Hereinafter the compound in question is named compound F.

The single FIGURE shows the drastic effect of compound F on morphine dependence.

Therefore, the aim of the present invention is to propose the use of compounds of formula (I), and especially of compound F, for the treatment of opiate drug dependence.

The impact of compounds with pharmacological activity of the 5-$HT_{1A}$ agonist type on the treatment of dependence on opiates was, up till now, non-existent. More particularly, while it is known that 5-$HT_{1A}$ agonists can exert pro-algesic as well as analgesic effects in some conditions and can counteract the pain relief induced by opiates (Millan et al, J. Pharmacol. Exp. Ther. 256(3), 983-992, 1991), it has never been proposed nor suggested, let alone demonstrated, that 5-$HT_{1A}$ agonists alleviate the specific pain that is paradoxically induced by opiates and that drives opiate drug addiction.

As the special pain/dysphoria induced by opiate-associated withdrawal is known to be a particular and difficult syndrome to treat, which is likely to require a special and high level of therapeutical efficacy, it is not obvious that a compound that is known to alleviate common pains (e.g., paracetamol, which counteracts the hyperalgesia induced by inflammatory agents) may at all be able to relieve opiate-induced pain/hyperalgesia.

Thus, the activity of compounds known for their role in analgesia, also called "antinociception", is not predictive of their possible effects on opiate-induced pain/hyperalgesia because the latter constitutes a special and extreme instance that is linked to the opiate psychological and physiological dependence phenomenon. Indeed, in spite of its wide and long-term availability, paracetamol for example does not treat opiate dependence.

With regard to 5-$HT_{1A}$ agonists, while it is known that 5-$HT_{1A}$ agonists can exert pro-algesic as well as analgesic effects in some conditions and while gepirone, for example, can counteract the pain relief induced by opiates (Millan and Colpaert, Neuropharmacology: 29: 315-318, 1990), gepirone, as shown below, does not counteract morphine-induced hyperalgesia.

The validity of animal models for studying the neurobiological and behavioural mechanisms involved in drug dependence date back to over twenty years of research. Several aspects of the behaviour of dependent individuals can thus be reproduced in the laboratory animal. For example, in the rat made dependent by chronic administration of morphine, the sudden interruption of morphine treatment or the administration of an antagonist of opiate receptors induces hyperalgesia, said state being easily evaluated by means of a variety of techniques that determine the emotional reaction to an aversive stimulation (Tilson et al., Psychopharmacol 28:297-300, 1973).

Contrary to morphine-induced analgesia, morphine-induced hyperalgesia is directly linked to the dependence phenomenon (Colpaert, Pharmacol Rev 48:355-342, 1996). Therefore, as previously mentioned, this state of hyperalgesia constitutes a sensitive, quantifiable, and widely recognised marker of opiate dependence. Consequently, the inventors chose to use such hyperalgesia as a first marker to evaluate the capacity of the compounds of the invention to oppose the appearance of a morphine dependence syndrome, the marker being used consisting of analysing the emotional reaction and vocalization to painful mechanical stimulation of the rat's hind paw (Randall-Selitto test). A second widely used test to address opiate drug addiction, namely intravenous opiate drug self-administration, was also used to test that capacity.

Compound F was compared with gepirone and lesopitron chosen as reference 5-HT$_{1A}$ agonists. Gepirone [83928-76-1], is a close structural analogue of buspirone [33386-08-2] and of tandospirone [112457-95-1], both of which are in clinical use for anxiety and depression. Lesopitron [132449-46-8] is the only 5-HT$_{1A}$ agonist to have been in clinical development for treating drug dependence (Pharmaprojects March 2001).

The results of the emotional-reaction Randall-Selitto test unambiguously show that:
i) morphine by itself reduced the threshold for the stimulation to elicit vocalization, thus indicating that morphine induced hyperalgesia;
ii) compound F by itself did not increase the threshold, thus indicating that it did not produce analgesia on its own in this test;
iii) when administered along with morphine, the reference 5-HT$_{1A}$ agonists (i.e., gepirone and lesopitron) did not have any detectable effect on the morphine-induced hyperalgesia, whereas,
iv) in contrast, compound F, when administered along with morphine, counteracted morphine-induced hyperalgesia, and the reaction threshold was then the same as that in normal (saline-treated) animals.

Thus, compound F prevents the occurrence of this particular and essential morphine withdrawal syndrome (namely hyperalgesia).

These results are novel. There is no prior evidence that a 5-HT$_{1A}$ agonist can prevent morphine-induced pain.

These results are also surprising in two ways. Firstly, it is known that 5-HT$_{1A}$ agonists among other things produce analgesia in some conditions. However, compound F, in particular as administered in exactly the same manner as when co-administered with morphine, does not produce analgesia in the condition of the emotional-reaction Randall-Selitto test. Secondly, it is known that 5-HT$_{1A}$ agonists among other things interact with opiates in a particular way; 5-HT$_{1A}$ agonists, among which gepirone, counteract opiate-induced pain relief (Millan and Colpaert, Neuropharmacology: 29: 315-318, 1990). However, compound F but not the reference 5-HT$_{1A}$ agonists, among which gepirone, prevents the occurrence of the morphine-induced pain.

Consequently, in spite of its inability to produce analgesia in the condition of the emotional-reaction Randall-Selitto test, and contrary to the reference compounds gepirone and lesopitron, compound F is capable of preventing and/or reducing opiate-induced pain (herein termed: "hyperalgesia") and thus preventing and/or reducing morphine dependence.

The results of the second widely used test to address opiate drug addiction, namely intravenous opiate drug (in particular: heroin) self-administration, confirming the findings cited above, unambiguously indicate that compound F counteracts intravenous heroin self-administration and that compound F is able to treat opiate dependence.

Thus, compound F is able to prevent and/or to treat the hyperalgesia, dysphoria and other signs of the sensory and affective/motivational dimensions of opiate-induced pain and consequently, the compelling drive to auto-medicate those signs.

Importantly, the present invention thus reveals the efficiency of compounds of formula (I), especially of compound F, for preventing and/or treating opiate-induced hyperalgesia, and consequently the craving for opiates.

As the craving is the psychological drive of opiate drug dependence, the subject-matter of the present invention is the method for preventing and/or treating opiate drug dependence comprising the administration of an effective amount of compounds of formula (I), especially of compound F, to a patient in need thereof.

At the least, the present invention concerns the method of reducing opiate drug dependence comprising the administration of an effective amount of compounds of formula (I), especially of compound F, to a patient in need thereof.

More particularly, as no tests have been conducted to address the physiological symptoms of the craving, results presented herein suggest the method of preventing and/or treating (at least reducing) the psychological craving for opiate, comprising the administration of compounds of formula (I), and especially of compound F, to a patient in need thereof.

Moreover, the present invention targets the method for preventing opiate drug dependence wherein the compounds of formula (I) are administered simultaneously, separately, or sequentially with an opiate drug to a patient in need thereof.

A further aim of the invention is pharmaceutical compositions containing as active principle at least one of the derivatives of general formula (I) or one of its salts or hydrates in combination with one or more pharmaceutically acceptable excipients or vehicles.

The pharmaceutical compositions according to the invention can, for example, be compositions administered by oral, nasal, sublingual, rectal or parenteral means. As an example of compositions able to be administered by oral means, pills, capsules, granules, powders and oral suspensions or solutions can be mentioned.

The appropriate formulations for the chosen method of administration are known and described, for example, in Remington, The Science and Practice of Pharmacy, 19th edition, 1995, Mack Publishing Company.

The effective dose of a compound according to the invention varies in function of numerous parameters such as, for example, the chosen administration method, the weight, age, sex, the substance or substances responsible for the pathology, and the sensitivity of the individual to be treated. Consequently, the optimal dose must be determined individually, in function of the relevant parameters, by a medical specialist. Even though the effective doses of a compound according to the invention can vary widely in proportion, the daily doses can be graduated between 0.01 mg and 100 mg per kg of body weight of the person under treatment. Nonetheless, one dose per day of a compound according to the invention, comprised between 0.10 mg and 100 mg per kg of body weight of the person being treated, is preferable.

When compound F is administered in association with other active substances, such as an opiate drug, compound F and the other active substances may be formulated as a mixture or separately in an identical or different form. They may be administered via the same or a different route (e.g. intravenously, orally, etc.).

The following examples serve to illustrate the pharmacological activity of the compound F and, therefore, its potential utility in the therapeutic aim claimed in the invention.

EXAMPLE 1

Measurement of the Affinity of Compound F for the 5-HT$_{1A}$ Receptor

Using rat cerebral cortex tissue, the study of the binding to the 5-HT$_{1A}$ receptor was carried out according to a standard method (Naunyn-Schmiedeberg's Arch. Pharmaco. 1991, 343, 106). The inhibition constant (Ki) of the product according to the invention was estimated from displacement experiments using the version 4 RADLIG non-linear regression programme of EBDA (Equilibrium Binding Data Analysis) (Biosoft, Cambridge, UK, Mc Pherson, 1985). The dissociation constant of the radioactive ligand (i.e., $^3$H-8-OH-DPAT) used in the calculations is 0.31 nmole. The value of pKi (−logKi) is provided under the form of the average of at least 3 experiments.

Results

The in vitro binding test indicates the pKi of compound F to be 9.07 and shows the compound to possess a high affinity for the serotonin receptor of sub-type 5-HT$_{1A}$.

EXAMPLE 2

Effects of Compound F and Reference Products on Morphine Dependence

1. Morphine-induced Enhanced Emotional Response/Hyperalgesia to Aversive, Nociceptive Stimulation The products are administered by means of osmotic mini-pumps (model 2ML2; flow rate 5 µl/hr: Alza Corporation, Palo Alto, USA) implanted subcutaneously on the first day of the experiment and extracted two weeks later. The pump is set in place through a transversal incision made in the skin of the dorsal face of the back of the rat, the liberation orifice being directed towards the head.

Morphine chlorhydrate is administered at 5 mg/rat/day (41.7 mg/ml) in solution in distilled water. Compound F is administered at 0.63 mg/rat/day (5.25 mg/ml) in solution in distilled water. Gepirone and lesopitron are administered at 2.5 mg/rat/day (20.8 mg/ml) in solution in distilled water. Naloxone (a µ-opiate receptor antagonist which induces a rapid non-natural withdrawal syndrome) is administered at 0.63 mg/kg by subcutaneous bolus injection. The doses refer to the weight of the non-salified agent. The pumps implanted in the control animals release 0.12 ml of 0.9% NaCl (saline)/rat/day.

The study consists of two phases: a phase of chronic treatment lasting 2 weeks, and a withdrawal phase lasting 4 days.

On the experiment's first day the rats were implanted with two osmotic mini-pumps. Six experimental groups received one of the following treatments: (a) pump 1=saline and pump 2=saline (n=11); (b) pump 1=saline and pump 2=compound F at 0.63 mg/rat/day (n=11); (c) pump 1=morphine at 5 mg/rat/day and pump 2=saline (n=13); (d) pump 1=morphine at 5 mg/rat/day and pump 2=compound F at 0.63 mg/rat/day (n=13); (e) pump 1=morphine at 5 mg/rat/day and pump 2=gepirone at 2.5 mg/rat/day (n=13); (f) pump 1=morphine at 5 mg/rat/day and pump 2=lesopitron at 2.5 mg/rat/day (n=13).

After two weeks of chronic infusions, the withdrawal phase began. After taking a baseline measurement on day 14, the animals received a sub-cutaneous bolus injection of either saline (group a) or 0.63 mg/kg of naloxone (all other groups). Next, measurements were made 30 minutes, 1 hr, 2 hr, 4 hr, and 8 hr after the bolus injection. The pumps were extracted after the last measurement at 8 hr after the naloxone injection. A series of further measurements was made daily, 24 hr to 4 days after the naloxone injection. Throughout, using the emotional-reaction Randall-Selitto test, the measurement consisted of determining the threshold value for mechanical stimulation to induce a vocalisation response. That is, increasing pressure is applied to the rat hind paw until the rat vocalizes; the pressure that is reached at that point defines the threshold (Randall and Selitto, Arch. Int. Pharmacodyn. 1957, 111, 409-419). The results are expressed in grams and a 750 g limit is imposed.

In order to evaluate the thresholds during the withdrawal phase (i.e., between 30 minutes and 4 days after the bolus injection of either saline in group a or naloxone in all other groups), the area under the curve (AUC) was determined for each rat individually using the day 14 baseline measurement as the reference; the AUCs were analysed statistically by analysis of variance (ANOVA). The post-hoc comparisons (i.e., those following the variance analysis when the latter is significant) were made using the Student-Newman-Keuls (SNK) test for comparing groups with each other. A statistically significant effect was defined as p<0.05. The AUCs that were thus obtained are shown in the graph in the appendix (single FIGURE).

Results

ANOVA analysis of these in vivo test data revealed significant treatment effects [F(5.68)=5.7; p<0.001]. The AUC values (see FIGURE) were significantly lower (SNK; p<0.05) in the animals that received morphine (and saline) plus the naloxone bolus injection compared to the animals that received saline (and saline) plus the saline bolus injection. The significant lowering of the vocalisation thresholds of the animals that received morphine shows that this syndrome can be objectified clearly by measuring the amplitude of the hyperalgesia which develops during the withdrawal phase.

The animals co-treated with both morphine and compound F, contrary to those treated by morphine alone and to those co-treated with morphine and gepirone (SNK; p<0.05) or morphine and lesopitron (SNK; p<0.05) have AUC values (SNK; p>0.05) statistically comparable with those obtained from the group of control animals that received no drug treatment at all. Compound F does not induce an effect on its own, as the comparable thresholds show (p>0.05) for control animals and those treated with compound F alone. It follows that only those animals co-treated by morphine and compound F did not demonstrate hyperalgesia and thus did not demonstrate this morphine withdrawal syndrome. The 5-HT$_{1A}$ reference agonists (i.e., gepirone and lesopitron) did not have any detectable effect on the morphine-induced hyperalgesia and thus on the morphine withdrawal syndrome. It thus follows that, contrary to the reference compounds, and in spite of the fact that it does not induce analgesia by itself in these conditions, compound F is potentially capable of counteracting opiate-induced pain (herein termed: "hyperalgesia") and thus preventing and reducing morphine dependence.

This study demonstrates that the compounds of formula (I) together with its addition salts with mineral acids or pharmaceutically acceptable organic acids are, contrary to the 5-HT$_{1A}$ agonists belonging to other chemical classes, useful in preventing opiate drug dependence.

2. Heroin Self-administration

To confirm the results with another well-established technique to assess opiate drug dependence, the effect of compound F on heroin self-administration was studied.

The experimental setting was similar to that which is typically used in rats (Ator and Griffiths, Drug Alcohol Dependence: 70: S55-S72, 2003). Briefly, partially food-deprived rats (n=11), previously implanted with an intravenous catheter for heroin intravenous administration, learned to self-administer heroin (0.02 mg/kg/injection) during daily 2-hour sessions. A single intravenous "priming" infusion was delivered by the experimenter at the start of each session. After responding for heroin had become stable (3 consecutive sessions during which the number of injections of heroin received per day did not vary by more than ±20%), saline and four different doses of compound F (i.e., 5 "test conditions") were tested in each rat using a Latin Square design. Saline or F compound (0.01, 0.04, 0.16 and 0.63 mg/kg) was administered by i.p. injection 15 minutes prior to the beginning of a heroin self administration test session.

For each test condition, the total number of infusions during the heroin self administration test session was recorded. Data are represented as the mean±SEM for each test condition.

Statistical analysis was conducted using analysis of variance with SAS V9.1, Mixed procedure followed by post hoc Dunnett test to assess the differences between saline and compound F. In all cases significance was defined as $p<0.05$.

Results

The obtained results are given in the table below.

| Treatment | Number of heroin injections (0.02 mg/kg/injection) per heroin session |
|---|---|
| Saline (i.p.) | 46.0 ± 29.7 |
| F 13640 (0.01 mg/kg, i.p.) | 40.2 ± 27.9 p > 0.05 |
| F 13640 (0.04 mg/kg, i.p.) | 31.5 ± 19.4 p > 0.05 |
| F 13640 (0.16 mg/kg, i.p.) | 9.3 ± 13.1 p < 0.001 |
| F 13640 (0.63 mg/kg, i.p.) | 8.4 ± 13.0 p < 0.001 |

ANOVA analysis of these in vivo test data revealed significant treatment effects [$F(4,39)=7.87$; $p<0.001$].

Compared with the number of heroin injections which the rats self-administered after a saline treatment before the test session, the number decreased as a function of the dose of the F compound and is approximately 5 times lower when compound F is administered at 0.16 mg/kg (post hoc analysis: $p<0.001$ for the 0.16 and 0.63 mg/kg doses).

Thus, it is shown here unambiguously that the compound F is able to inhibit the seeking of heroin in rats that intravenously self-administer the opiate heroin.

As it is well known that a high level of opiate self-administration is a marker of high opiate dependency, these results show that the administration of compound F is able to treat opiate dependence.

Thus, compound F is able to counteract the hyperalgesia, dysphoria and other signs of the sensory and affective/motivational dimensions of opiate-induced pain and consequently, to reduce and abolishe the compelling drive (other descriptions refer to "craving") to auto-medicate those signs by means opiate self-administration.

This result unambiguously indicates that compound F counteracts intravenous heroin self-administration and therefore is able to treat opiate dependence.

The invention claimed is:

1. A method for treating opiate drug dependence, comprising administering an effective amount of at least one compound of formula (I):

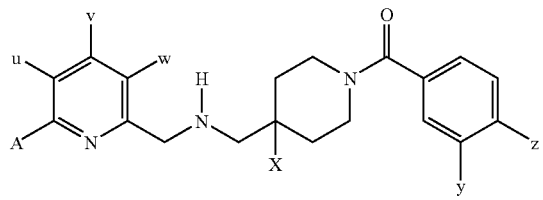

(I)

and/or its therapeutically acceptable salts, with pharmaceutically acceptable organic or mineral acids, to a patient in need thereof in which:
u represents a hydrogen atom or a methyl radical, with the proviso that when u is a methyl radical then v and w represent a hydrogen atom;
v represents a hydrogen atom, a chlorine atom or a methyl radical, with the proviso that when v is a methyl radical then u and w represent a hydrogen atom;
w represents a hydrogen atom, a fluorine atom or a methyl radical, with the proviso that when w is a methyl radical then u and v represent a hydrogen atom;
x represents a hydrogen atom or a fluorine atom;
y represents a chlorine atom or a methyl radical;
z represents a hydrogen atom, a fluorine atom, a chlorine atom or a methyl radical;
A represents:
  a. a hydrogen atom, a fluorine atom or a chlorine atom;
  b. a straight or branched chain saturated aliphatic hydrocarbon radical having from 1 to 5 carbon atoms;
  c. a fluoroalkyl radical;
  d. a cyclopropyl, cyclobutyl or cyclopentyl radical;
  e. a 5-membered aromatic heterocyclic group, substituted or not, having 1, 2, 3 or 4 heteroatoms selected from the group consisting of nitrogen, oxygen and sulfur, wherein at most one oxygen and/or one sulfur atom is present in the 5-membered heterocyclic group;
  f. an alkoxy ($R_1O$—) or alkylthio ($R_1S$—) group in which the $R_1$ radical represents:
    (1) an alkyl radical in $C_1$-$C_5$ as defined above;
    (2) a monofluoromethyl or trifluoromethyl radical;
    (3) a cyclopropyl, cyclobutyl or cyclopentyl radical;
    (4) an amino group of formula (II):

(II)

in which $R_2$ and $R_3$, which may be identical or different, represent hydrogen, a straight or branched chain saturated aliphatic hydrocarbon radical having from 1 to 5 carbon atoms, a cyclopropyl group or a trifluoromethyl group;
    (5) a saturated cyclic amino group of formula (III):

(III)

in which n is 1 or 2; or
    (6) an alkoxycarbonyl group.

2. The method of claim 1, wherein A represents a straight or branched chain saturated aliphatic hydrocarbon radical having from 1 to 5 carbon atoms selected from the group consisting of methyl, ethyl, propyl, butyl, pentyl, isopropyl, 1-methyl-ethyl, 1-methyl-propyl, 1-methyl-butyl, 2-methyl-propyl, 2-methyl-butyl, 3-methyl-butyl, 1-ethyl-propyl and 2-ethyl-propyl.

3. The method of claim 1, wherein A represents a fluoroalkyl radical selected from the group consisting of monofluoromethyl (—$CH_2F$), difluoromethyl (—$CHF_2$), trifluoromethyl (—$CF_3$), 1-fluoro-1-ethyl (—$CHFCH_3$) and 1,1-difluoro-1-ethyl (—$CF_2CH_3$).

4. The method of claim 1, wherein A represents a methoxycarbonyl group (CH₃OCO—) or an ethoxycarbonyl (CH₃CH₂OCO—) group.

5. The method of treating opiate drug dependence according to claim 1, where in the compound of formula (I), A represents a hydrogen atom, u represents a methyl radical, v and n each represent a hydrogen atom, x represents a fluorine atom, y represents a chlorine atom and z represents a fluorine atom.

6. A method for treating hyperalgesia induced by opiate drug withdrawal, comprising administering an effective amount of at least one compound of formula (I):

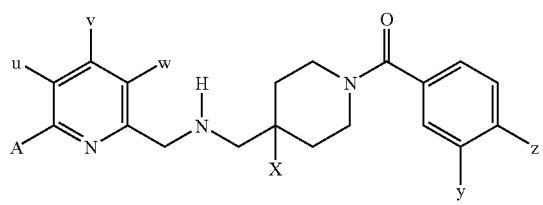

and/or its therapeutically acceptable salts, with pharmaceutically acceptable organic or mineral acids, to a patient in need thereof in which:

u represents a hydrogen atom or a methyl radical, with the proviso that when u is a methyl radical then v and w represent a hydrogen atom;

v represents a hydrogen atom, a chlorine atom or a methyl radical, with the proviso that when v is a methyl radical then u and w represent a hydrogen atom;

w represents a hydrogen atom, a fluorine atom or a methyl radical, with the proviso that when w is a methyl radical then u and v represent a hydrogen atom;

x represents a hydrogen atom or a fluorine atom;

y represents a chlorine atom or a methyl radical;

z represents a hydrogen atom, a fluorine atom, a chlorine atom or a methyl radical;

A represents:
  a. a hydrogen atom, a fluorine atom or a chlorine atom;
  b. a straight or branched chain saturated aliphatic hydrocarbon radical having from 1 to 5 carbon atoms;
  c. a fluoroalkyl radical;
  d. a cyclopropyl, cyclobutyl or cyclopentyl radical;
  e. a 5-membered aromatic heterocyclic group, substituted or not, having 1, 2, 3 or 4 heteroatoms selected from the group consisting of nitrogen, oxygen and sulfur, wherein at most one oxygen and/or one sulfur atom is present in the 5-membered heterocyclic group;
  f. an alkoxy (R₁O—) or alkylthio (R₁S—) group in which the R₁ radical represents:
    (1) an alkyl radical in C₁-C₅ as defined above;
    (2) a monofluoromethyl or trifluoromethyl radical;
    (3) a cyclopropyl, cyclobutyl or cyclopentyl radical;
    (4) an amino group of formula (II):

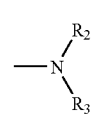

in which R₂ and R₃, which may be identical or different, represent hydrogen, a straight or branched chain saturated aliphatic hydrocarbon radical having from 1 to 5 carbon atoms, a cyclopropyl group or a trifluoromethyl group;
    (5) a saturated cyclic amino group of formula (III):

in which n is 1 or 2; or
  (6) an alkoxycarbonyl group.

7. The method for treating hyperalgesia induced by opiate drug withdrawal according to claim 6, where in the compound of formula (I), A represents a hydrogen atom, u represents a methyl radical, v and n each represent a hydrogen atom, x represents a fluorine atom, y represents a chlorine atom and z represents a fluorine atom.

8. A method for treating psychological craving induced by opiate drug withdrawal, comprising the administration of an effective amount of compounds of formula (I)

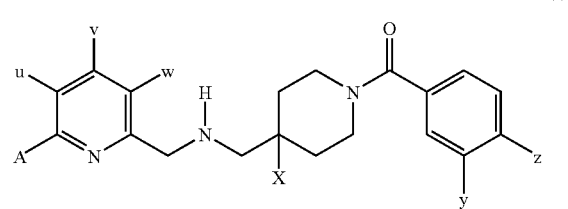

and/or its therapeutically acceptable salts, with pharmaceutically acceptable organic or mineral acids, to a patient in need thereof in which:

u represents a hydrogen atom or a methyl radical, with the proviso that when u is a methyl radical then v and w represent a hydrogen atom;

v represents a hydrogen atom, a chlorine atom or a methyl radical, with the proviso that when v is a methyl radical then u and w represent a hydrogen atom;

w represents a hydrogen atom, a fluorine atom or a methyl radical, with the proviso that when w is a methyl radical then u and v represent a hydrogen atom;

x represents a hydrogen atom or a fluorine atom;

y represents a chlorine atom or a methyl radical;

z represents a hydrogen atom, a fluorine atom, a chlorine atom or a methyl radical;

A represents:
  a. a hydrogen atom, a fluorine atom or a chlorine atom;
  b. a straight or branched chain saturated aliphatic hydrocarbon radical having from 1 to 5 carbon atoms;
  c. a fluoroalkyl radical;
  d. a cyclopropyl, cyclobutyl or cyclopentyl radical;

e. a 5-membered aromatic heterocyclic group, substituted or not, having 1, 2, 3 or 4 heteroatoms selected from the group consisting of nitrogen, oxygen and sulfur, wherein at most one oxygen and/or one sulfur atom is present in the 5-membered heterocyclic group;
f. an alkoxy ($R_1O$—) or alkylthio ($R_1S$—) group in which the $R_1$ radical represents:
(1) an alkyl radical in $C_1$-$C_5$ as defined above;
(2) a monofluoromethyl or trifluoromethyl radical;
(3) a cyclopropyl, cyclobutyl or cyclopentyl radical;
(4) an amino group of formula (II):

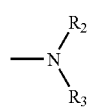

(II)

in which $R_2$ and $R_3$, which may be identical or different, represent hydrogen, a straight or branched chain saturated aliphatic hydrocarbon radical having from 1 to 5 carbon atoms, a cyclopropyl group or a trifluoromethyl group;
(5) a saturated cyclic amino group of formula (III):

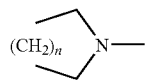

(III)

in which n is 1 or 2; or
(6) an alkoxycarbonyl group.

9. Method for treating psychological craving induced by opiate drug withdrawal according to claim 8, where in the compound of formula (I), A represents a hydrogen atom, u represents a methyl radical, v and n each represent a hydrogen atom, x represents a fluorine atom, y represents a chlorine atom and z represents a fluorine atom.

10. The method for treating opiate drug dependence of claim 1, wherein the at least one compound of formula (I) is administered simultaneously, separately, or sequentially with an opiate drug to a patient in need thereof.

11. The method for treating opiate drug dependence of claim 10, where in the compound of formula (I), A represents a hydrogen atom, u represents a methyl radical, v and n each represent a hydrogen atom, x represents a fluorine atom, y represents a chlorine atom and z represents a fluorine atom.

12. The method of claim 6, wherein said method treats the symptoms of hyperalgesia induced by opiate drug withdrawal by reducing the reaction threshold for pain to normal levels.

13. The method of claim 8, wherein said method treats the symptoms of hyperalgesia induced by opiate drug withdrawal by reducing the reaction threshold for pain to normal levels.

14. The method of claim 1, where in the compound of formula (I) A=H, u=CH3, v=H, w=H, X=f, y=Cl and z=F.

15. The method of claim 6, where in the compound of formula (I) A=H, u=CH3, v=H, w=H, X=f, y=Cl and z=F.

16. The method of claim 8, where in the compound of formula (I) A=H, u=CH3, v=H, w=H, X=f, y=Cl and z=F.

* * * * *